(12) United States Patent
Ueno et al.

(10) Patent No.: US 7,183,428 B2
(45) Date of Patent: Feb. 27, 2007

(54) METHOD FOR PRODUCTION OF ACRYLIC ACID

(75) Inventors: Kouji Ueno, Himeji (JP); Harunori Hirao, Himeji (JP); Naoki Serata, Himeji (JP); Takeshi Yokogoshiya, Himeji (JP)

(73) Assignee: Nippon Shokubai Co., Inc., Osaka (JP)

( * ) Notice: Subject to any disclaimer, the term of this patent is extended or adjusted under 35 U.S.C. 154(b) by 0 days.

(21) Appl. No.: 10/858,935

(22) Filed: Jun. 2, 2004

(65) Prior Publication Data
US 2004/0249199 A1 Dec. 9, 2004

(30) Foreign Application Priority Data
Jun. 5, 2003 (JP) ............................. 2003-160773

(51) Int. Cl.
*C07C 51/16* (2006.01)
*C07C 51/42* (2006.01)

(52) U.S. Cl. ............... 562/545; 562/521; 562/532; 562/542; 562/600

(58) Field of Classification Search ........ 562/600, 562/521, 532, 542, 545
See application file for complete search history.

(56) References Cited

U.S. PATENT DOCUMENTS

| 4,317,926 | A | 3/1982 | Sato et al. ............... 562/532 |
|---|---|---|---|
| 5,831,124 | A | 11/1998 | Machhammer et al. ..... 562/600 |
| 6,252,110 | B1 | 6/2001 | Uemura et al. ............. 562/598 |
| 6,433,222 | B1 | 8/2002 | Eck et al. .................... 562/600 |
| 6,448,439 | B1 | 9/2002 | Eck et al. .................... 562/600 |
| 6,482,981 | B2 * | 11/2002 | Ueno et al. .................. 562/600 |
| 6,498,272 | B1 | 12/2002 | Schroder et al. ............ 562/600 |
| 6,541,665 | B1 | 4/2003 | Bastiaensen et al. ........ 562/600 |
| 6,596,901 | B1 | 7/2003 | Eck et al. .................... 562/600 |
| 6,599,397 | B2 | 7/2003 | Sakamoto et al. ............. 203/8 |
| 6,679,939 | B1 | 1/2004 | Thiel et al. .................... 95/210 |
| 2003/0028051 | A1 | 2/2003 | Shlbusawa et al. |

FOREIGN PATENT DOCUMENTS

| DE | 19838845 A1 | 8/1998 |
|---|---|---|
| EP | 1116709 A1 | 1/2001 |
| JP | 2001-348359 | 12/2001 |

\* cited by examiner

*Primary Examiner*—Taylor Victor Oh
(74) *Attorney, Agent, or Firm*—Mathews, Shepherd, McKay & Bruneau, P.A.

(57) ABSTRACT

A method for producing acrylic acid by using an acrylic acid-containing solution of high concentration without azeotropic distillation is provided. This method of producing acrylic acid comprises introducing an acrylic acid-containing gas obtained by catalytic gas phase oxidation reaction into an absorption column and supplying the acrylic acid-containing solution to crystallization step thereby separating the solution into acrylic acid and residual mother liquid, and distilling at least part of the residual mother liquid and circulating the distillate obtained by the distillation to the absorption column.

7 Claims, 2 Drawing Sheets

METHOD FOR PRODUCTION OF ACRYLIC ACID

BACKGROUND OF THE INVENTION

1. Field of the Invention

This invention relates to a method for producing acrylic acid in a high yield by subjecting an acrylic acid-containing solution obtained by absorption with water to a crystallizing step thereby obtaining acrylic acid crystals and a crystal mother liquid, and circulating the crystal mother liquid to an absorption column thereby enhancing the absorption ratio of acrylic acid.

2. Description of the Related Art

Commercial production of acrylic acid generally resorts to the method of propylene oxidation which consists in subjecting propylene and/or acrolein to catalytic gas phase oxidation. When acrylic acid is produced by this method of propylene oxidation, the step of propylene oxidation gives rise to such impurities as water, acids like propionic acid, acetic acid, and maleic acid, and aldehydes like acetone, acrolein, furfural, and formaldehyde in the form of by-products. The gas containing these by-products is absorbed as an acrylic acid-containing solution generally via contact with an absorbent and obtained the solution is subsequently separated by distillation etc.

One known method, for example, produces acrylic acid of high purity by absorbing an acrylic acid-containing gas resulting from catalytic gas phase oxidation with a high boiling solvent, distilling the acrylic acid-containing solution thereby separating it into the solvent and crude acrylic acid, and subsequently subjecting the crude acrylic acid to a process of crystallization (JP-A-1997-227445). By this method, the residual acrylic acid-containing gas which has escaped absorption by a high boiling solvent is cooled and transformed into a condensate containing water, formaldehyde, and acetic acid and the condensate is discarded to the out side of system. Further, by circulating the crystal mother liquid to the absorption column, the separation of covariant components by the scrapping of a low boiling substance and the stripping of a low boiling substance is enhanced.

Certain known methods produce acrylic acid by directly crystallizing the condensate obtained by condensing an acrylic acid-containing gas (the official gazettes of International Unexamined Patent Publication JP-2000-514077, JP-2001-516736, and JP-2002-521353). When the solution is cooled at the crystallizing step in the absence of an organic solvent or an extracting agent, the crystals are solidified instead of being precipitated. Thus, an organic solvent has been hitherto used to avoid this solidification. It has been found that acrylic acid can be directly crystallized from the condensate of an acrylic acid-containing gas. These methods have been perfected based on this knowledge. They are characterized by obviating the necessity of adding a supplementary substance. The method of the JP-2000-514077 circulates part of the crystal mother liquid to the crystallizing step and the method of the JP-2001-516736 and the JP-2002-521353 resort to fractional condensation of the pertinent components in contrast to the ordinary condensation. Specifically, they separate acrylic acid as an intermediate boiling fraction, discard an acrylic acid-containing low boiling fraction as waste water, and recirculate part of an acrylic acid-containing high boiling fraction and discard the remainder thereof.

A known method produces acrylic acid by suddenly cooling an acrylic acid-containing gas as with a spray cooling device, further condensing the quenched gas thereby forming crude acrylic acid, and crystallizing the crude acrylic acid (the official gazette of International Unexamined Patent Publication 2002-539104). This method has been perfected with a view to effectively utilizing an acrylic acid oligomer which occurs during the step of acrylic acid production. It uses acrylic acid oligomer-containing bottom liquid of a separation column as a quenching liquid for an acrylic acid-containing gas, withdraws part of the quenching liquid as an effusion and decomposes the acrylic acid oligomer into acrylic acid, condenses the resultant acrylic acid, and use the resultant condensate as a quenching liquid.

A method for producing acrylic acid while embracing a process of distilling the mother liquid obtained during crystallization of an acrylic acid-containing mixture thereby obtaining a residue of distillation and a column top product and recrystallizing part of the column top product has been disclosed (the official gazette of International Unexamined Patent Publication JP-2002-519402). This method is aimed at exalting the purity of acrylic acid by distilling at least part of the mother liquid occurring during first crystallization, crystallizing the column top product formed during the distillation, returning the resultant crystals to the first crystallization, and discarding the residue of crystallization to the out side of system.

When an aqueous solution can be used as an absorbent for acrylic acid in the place of an expensive high boiling solvent, the use of this aqueous solution proves economical. Particularly, when this aqueous solution is capable of absorbing the acrylic acid-containing solution in high concentration, the use of the aqueous solution is efficient in respect that it results in decreasing the amount of treatment at the subsequent steps of purification. Thus, a method which, in absorbing in an aqueous solution an acrylic acid-containing gas formed by the reaction of catalytic gas phase oxidation, supplies the recovered water emanating from a step of azeotropic dehydration to an absorption column, supplies the acrylic acid-containing solution consequently formed to a stripping column, and obtains an acrylic acid-containing solution containing 70.9 wt. % of acrylic acid, 25.6 wt. % of water, and 2.0 wt. % of acetic acid from the bottom of the stripping column has been proposed (JP-A-2001-199931). This method obtains purified acrylic acid by subjecting the acrylic acid-containing solution to azeotropic dehydration and subsequently to a step of crystallization.

The methods disclosed in the patent documents mentioned above, however, require an expensive organic solvent and consequently entail the necessity of performing such an extra operation as re-purification of the used organic solvent (JP-A-1997-227446 and JP-A-2001-199931) or carrying out complicated fractional condensation different from ordinary condensation and liable to add to the cost of equipment. Further, since the separated fractions different from the target components are discharged from the system notwithstanding they contain acrylic acid in considerable amounts, the yield of purification incurs a decline and the fractions mentioned above demand a treatment of waste disposal (the official gazettes of International Unexamined Patent Publication JP-2001-516736, JP-2002-521353, and JP-2002-539104).

Under these existing circumstances, the development of a method for producing acrylic acid of high purity in a high yield by the use of a simple apparatus has been yearned for.

SUMMARY OF THE INVENTION

The present inventor has found that an acrylic acid-containing solution obtained by using an absorbing aqueous solution during the production of acrylic acid can be subjected in an unmodified form to a crystallizing treatment, that the residual mother liquid obtained during the step of crystallization can be enabled to enhance the absorption ratio of acrylic acid by being circulated to the absorption column, and that the acrylic acid loss can be consequently allayed. This invention has been perfected on the basis of this knowledge.

According to this invention, the acrylic acid-containing solution absorbed with water can be treated by a process of crystallization with the object of producing acrylic acid and without undergoing a process of azeotropic dehydration meantime.

This invention befits purification of an acrylic acid-containing solution having a particularly high acrylic acid concentration. The acrylic acid of a high concentration such as this can be obtained by distilling the residual mother liquid obtained by the process of crystallization and circulating the resultant distillate to an absorption column. This invention provides a method for producing acrylic acid expeditiously with a high efficiency of production while allaying the acrylic acid loss. Now, it will be described in detail below.

DESCRIPTION OF THE PREFERRED EMBODIMENT

Figure 1:
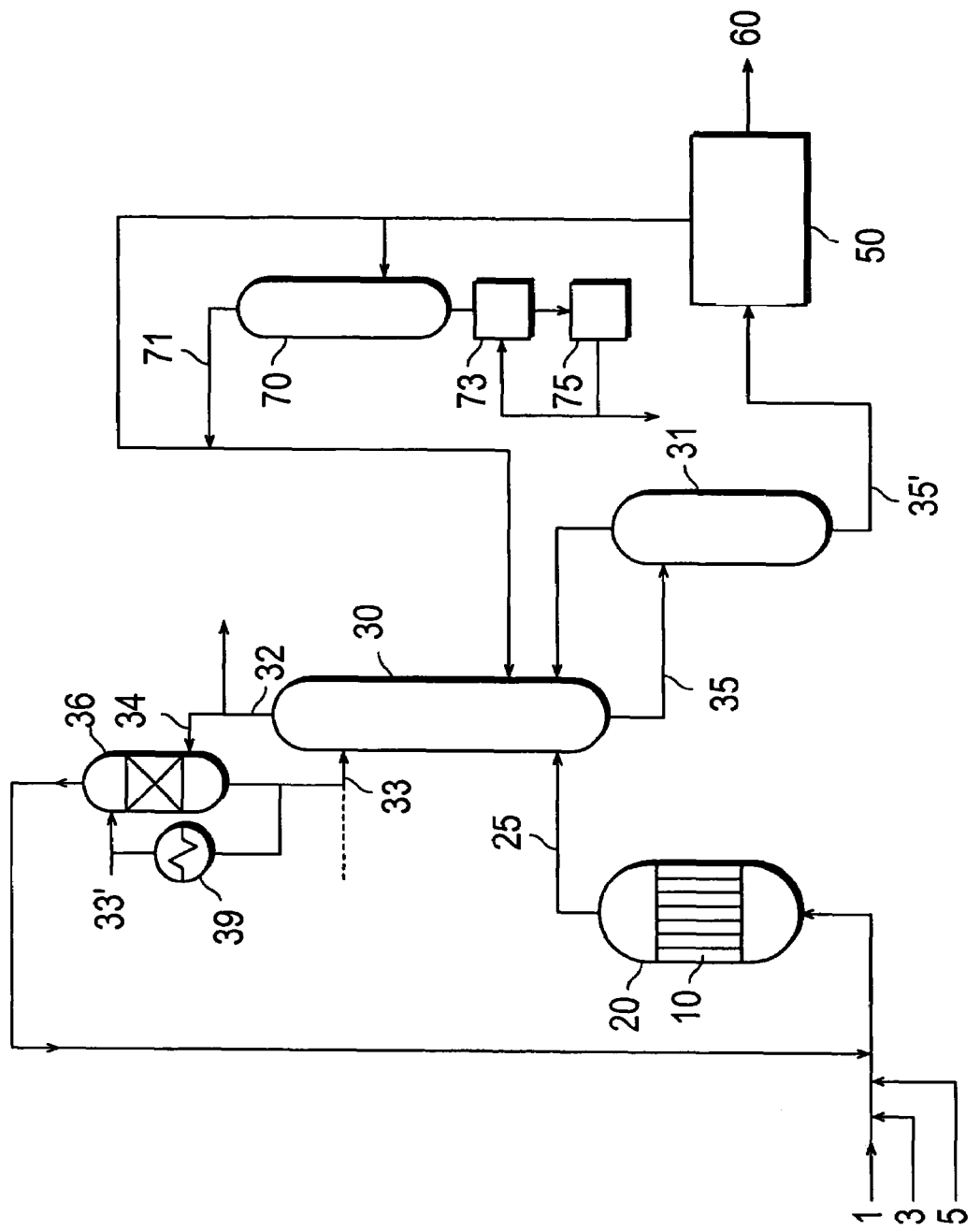
FIG. 1 is a process diagram illustrating one example of the preferred mode of embodying this invention.

The first aspect of this invention is directed toward a method for producing acrylic acid, characterized by comprising a) a step of introducing an acrylic acid-containing gas obtained by the reaction of catalytic gas phase oxidation of raw material of acrylic acid into an absorption column, causing it to contact with an absorbing aqueous solution, and consequently obtaining an acrylic acid-containing solution, b) a step of supplying the acrylic acid-containing solution to a crystallizing step and consequently separating it into acrylic acid and a residual mother liquid, and c) a step of subjecting at least part of the residual mother liquid to a distilling and circulating the distillate obtained by the distilling to the absorption column of the step a) mentioned above.

The characteristic feature of this invention resides in performing a crystallizing treatment on the acrylic acid-containing solution absorbed with the aqueous solution, distilling the residual mother liquid obtained during the crystallizing treatment, and circulating the resultant distillate to the absorption column. The practice of adding a salt to the acrylic acid-containing solution for the purpose of decomposing an acrylic acid-containing water/acrylic acid eutectic system, treating the solution prior to the crystallizing step for the purpose of expelling the effect of the contained water on the crystallizing treatment, and performing the crystallizing treatment after a low boiling substance and a high boiling substance have been removed in advance has prevailed hitherto. This invention, however, enables acrylic acid of high purity to be produced by a simple process by using an acrylic acid-containing solution obtained by absorbing an acrylic acid-containing gas with an aqueous solution, namely an acrylic acid-containing solution prior to the removal of water and high boiling substance, subjecting the solution in an unmodified form to a crystallizing treatment, distilling the residual mother liquid occurring during the crystallizing treatment, and circulating the resultant distillate to the absorption column. Moreover, the distillate containing water and acetic acid can be obtained by distilling the residual mother liquid obtained during the crystallizing treatment and the absorption efficiency of acrylic acid can be enhanced by circulating the distillate to the absorption column. Additionally, it can prevent high boiling substance from concentration in the absorption column and enhance the concentration of acrylic acid in bottom liquid of the absorption column. Further, such effective components as acrylic acid dimer which are contained in the residual mother liquid can be decomposed into acrylic acid by performing a step of decomposing acrylic acid dimer. When the product of this decomposition is circulated to the distillation column, it is automatically circulated to the absorption column and eventually crystallized and recovered as a finished product of acrylic acid. One example of the preferred mode of embodying this invention will be described below based on FIG. 1.

First, such a molecular oxygen-containing gas as air 3, the raw material of acrylic acid 1 such as propylene and/or acrolein, and a diluting gas 5 are mixed together. At this step, a recycle gas 34 which has undergone the acrylic acid absorbing step and subsequently discharged through the top of the absorption column may be mixed with the air, propylene and/or acrolein, and diluting gas. In this case, the recycle gas 34 may be used as a diluting gas. This mixed gas (hereinafter referred to occasionally as "the raw material gas") is supplied to a reactor 20 packed with a catalyst 10 for catalytic gas phase oxidation and subjected therein to a reaction of catalytic gas phase oxidation to obtain an acrylic acid-containing gas 25. The gas 25 is supplied to an absorption column 30 via the bottom thereof and the absorbing aqueous solution 33 is supplied to the absorption column 30 via the top thereof, with the result that the acrylic acid-containing gas 25 and the absorbing aqueous gas 33 will be brought into mutual contact. To the absorption column 30, an distillate 71 from a distillation column 70 which will be described specifically herein below and the residual mother liquid from a crystallizing device 50 mentioned below are supplied. Of the discharged gas 32 from the top of the absorption column 30, only the recycle gas 34 is introduced into a cooling column 36 and cooled therein by gas-liquid contact with the absorbing water 33' supplied anew into the system so as to induce condensation of a condensable substance contained in the recycle gas 34 and thereafter circulated to the reactor 20. The resultant condensate may be mixed with the absorbing water 33' and supplied as an absorbing aqueous solution 33 to the absorption column 30. In this specification, the part of a discharged gas 32 from the top of the absorption column 30, namely the exhaust gas circulated to the reactor will be referred to as "a recycle gas" and the part thereof, namely the gas discarded to the out side of system will be referred to as "a waste gas." By circulating the distillate 71 of the distillation column in the manner described above and cooling the recycle gas 34 as well, it is made possible to obtain the acrylic acid-containing solution 35 containing acrylic acid in a high concentration via the bottom of the absorption column.

The acrylic acid-containing solution 35 is supplied to an acrolein separation column 31 and treated therein for separation of acrolein contained therein, with the result that an acrylic acid-containing solution 35' having a lowered acrolein content is obtained via the bottom of the column. When the column top distillate of the separation column 31 is circulated to the bottom of the absorption column 30, the acrylic acid distilled out in conjunction with acrolein can be effectively recovered.

Then, acrylic acid as a finished product 60 is obtained when the acrylic acid-containing solution 35' is supplied to the crystallizing device 50. Meanwhile, at least part of the residual mother liquid from the crystallizing device 50 is supplied to the intermediate stage of the distillation column 70 to induce distillation of the low boiling substance and acrylic acid contained therein through the column top and the distillate 71 is circulated to the absorption column 30 mentioned above. The remainder of the residual mother liquid is directly circulated to the absorption column 30. Since the high boiling substance contained in the bottom liquid of the distillation column 70 contains acrylic acid dimer, the bottom liquid is advanced through a thin layer evaporator 73 and retained in a dimer decomposing tank 75 so as to be thermally decomposed into acrylic acid. When this acrylic acid is returned to the thin layer evaporator 73, it is transformed into a distillate 71 emanating from the top of the distillation column 70. When the distillate 71 is circulated to the absorption column 30, it can be finally recovered as the finished product of acrylic acid 60.

The characteristic feature of this invention resides in subjecting the acrylic acid-containing solution obtained by the absorption with the aqueous solution mentioned above to the crystallizing treatment either in its unmodified form or after it has been deprived of the contained acrolein by the treatment for separation of acrolein. The acrylic acid content of the solution, therefore, is commendably expected to be not less than 80 wt. %, preferably not less than 85 wt. %, and particularly not less than 87 wt. %. If the acrylic acid content falls short of 80 wt. %, the shortage will result in increasing the number of cycles of crystallization performed for obtaining acrylic acid crystals by the treatment of crystallization and complicating the operation. This invention provides a method for producing acrylic acid expeditiously in high yield while avoiding a step of azeotropically dehydrating such low boiling substances as water and a step of recovering a solvent and allaying the acrylic acid loss.

In the present specification, the term "low boiling substance" refers to a substance having a lower boiling point than acrylic acid in the normal state and the term "high boiling substance" refers to a substance having a higher boiling point than acrylic acid in the normal state. The term "condensable substance" refers to a substance which is a liquid under the atmospheric pressure, the term "distillation" refers to an operation of heating a solution to the boiling point thereof so as to separate a volatile component contained therein, the term "stripping" refers to an operation of supplying a stripping gas into a solution so as to migrate a target substance in the solution to the gas phase, and the term "crystallization" refers to an operation of producing crystals from the liquid phase and the gas phase. Then, the term "step of dynamic crystallization" refers to a method of crystallization for moving the liquid phase with the forced convection caused by means of a pump etc. during the course of crystallization and the term "step of static crystallization" refers to a method of crystallization for moving the liquid phase solely by spontaneous convection without using a pump, for example.

(1) Step of Absorbing Acrylic Acid

To obtain an acrylic acid-containing solution of high concentration, it is necessary either to decrease the amount of a water component introduced into the system or increase the amount of a water component discarded out of the system. For the purpose of minimizing the acrylic acid loss discharged out of the system, it is proper to recycle the discharged gas emanating from the top of the absorption column to the reactor. This invention, by cooling the recycle gas thereby decreasing the amount of the water component contained therein and thereafter advancing it to the reactor, is enabled to decrease the amount of the water component introduced into the absorption column, decrease the acrylic acid loss, and obtain the acrylic acid-containing solution of high concentration. When the whole amount of the discharged gas of the absorption column is cooled so as to decrease the amount of the water component and the amount of a low boiling substance which are discarded in the form of a gas out of the system, the amount of the water component in the recycle gas is decreased and yet the absorption efficiency of acrylic is not enhanced but is heavily degraded more than when the cooling is omitted and, moreover, the low boiling substance is concentrated within the system. When the condensate formed by the cooling is withdrawn out of the system, there ensues the necessity of disposing of a large amount of waste liquid. Thus, it is advisable to cool only the part of the gas discharged from the acrylic acid absorption column which is recycled to the reactor, namely the so-called recycle gas. Further, by cooling the recycle gas, it is made possible to condense not only the water component but also the acid component, decrease the acid component supplied to the reactor, and prevent the catalyst from being deteriorated by the acid. The condensate formed by the cooling may be either returned to the absorption column or withdrawn from the system instead of being returned to the absorption column. Though the acrylic acid loss ratio is not changed very much between these two choices and the amount of the waste liquid is extremely small, the return of the whole amount to the absorption column is at an advantage in obviating the necessity of disposal of waste liquid. Incidentally, the decrease of the amount of the water component introduced into the system may be attained by depriving the molecular oxygen-containing gas being supplied to the reactor of the water component before it is advanced to the reactor.

In this invention, propylene and/or acrolein can be used as the raw material gas of acrylic acid. While the reactor 20 does not need to be particularly restricted but is only required to be capable of performing a reaction of catalytic gas phase oxidation. The shell-and-tube type reactor can be used advantageously in respect that it excels in the efficiency of reaction. By packing the reactor 20 with the well-known catalyst 10 for catalytic gas phase oxidation and then bringing the raw material gas into contact with such a molecular oxygen-containing gas as oxygen or air, it is made possible to effect the oxidation of the raw material gas. When propylene is used as the raw material gas, the propylene concentration is in the range of 7–15 vol %, water concentration in the range of 0–10 vol. %, and the molecular oxygen concentration is such that the ratio of propylene: molecular oxygen (by volume) falls in the range of 1:1.0–2.0. Air may be used as the source of supply of molecular oxygen. When the air contains a water component, it is preferred to be dehumidified prior to the supply thereof to the reactor. The dehumidification is preferred because it is capable of decreasing the amount of water introduced into the reactor and consequently decreasing the amount of water introduced to the absorption column. It is permissible to use an oxygen-enriched air or purified oxygen in the place of air. As concrete examples of the diluting gas 5, nitrogen, carbon dioxide, and other inert gases may be cited.

In this invention, the recycle gas may be introduced into the reactor after it has been cooled to induce condensation of a condensable substance. When the recycle gas is used in this manner, the recycle gas is deprived of the water component in advance so that the water concentration in the raw material gas supplied to the reactor falls in the range of 0–10 vol %, preferably in the range of 0–7 vol %, and particularly in the range of 0–6 vol %. If the concentration exceeds 10 vol %, the excess will possibly result in causing the water component supplied via the reactor to the absorption column to increase the acrylic acid loss ratio. The total acid concentration is so adjusted at to fall in the range of 0–0.2 vol % and more preferably in the range of 0–0.1 vol %. If the total acid concentration exceeds 0.2 vol %, the excess will possibly result in accelerating the deterioration of the catalyst by oxidation. The recycle gas contains unaltered propylene and acrolien, oxygen, diluting gas, etc. in addition to the water component and the acid component. The propylene, oxygen, water component concentration, and total acid concentration mentioned above can be easily adjusted by computing the amount of the water component contained in the recycle gas and the amount thereof to be incorporated in the raw material gas so as to enable the water component concentration and the total acid concentration in the raw material gas to fall in the optimum ranges mentioned above and computing the propylene concentration and the oxygen concentration in the recycle gas thereby deciding the amount of propylene and the amount of air to be newly supplied to the reactor. The term "total acid" as used herein refers to compounds having a carboxyl group. The recycle gas contains acrylic acid, formic acid, and acetic acid as compounds answering the description.

The reaction of catalytic gas phase oxidation performed by using propylene as the raw material is generally carried out in two stages by the use of two kinds of catalyst 10 for catalytic gas phase oxidation. The catalyst for the first stage of this reaction is capable of forming acrolein mainly by the gas phase oxidation of the raw material gas containing propylene in a gas phase and the catalyst for the second stage of the reaction is capable of forming acrylic acid mainly by the gas phase oxidation of the raw material containing acrolein. As the catalyst for the first stage of the reaction, a complex oxide containing iron, molybdenum, and bismuth may be cited. As the catalyst for the second stage of the reaction, a catalyst having vanadium as an essential component may be cited.

FIG. 1 depicts the mode of performing the two-stage reaction mentioned above with a single reactor. Optionally, these reactions may be performed in a tandem system having two different reactors connected to each other. The acrylic acid-containing gas 25 which is obtained by the reaction of catalytic gas phase oxidation contains 5–14 vol % of acrylic acid, 0.1–2.5 vol % of acetic acid, 0.5–3 vol % of molecular oxygen, and 5–36 vol % of water and other components which are by-products of reaction such as the unaltered component of the raw material gas, propionic acid, maleic acid, acetone, acrolein, furfural, formaldehyde and $CO_x$.

In the acrylic acid absorption column 30, any of the known methods of contact may be used for establishing contact between the acrylic acid-containing gas and the absorbing aqueous solution. As concrete examples of such methods of contact, crossflow contact devices using a bubble-cap tray, a uniflat tray, a perforated tray, a jet tray, a valve tray, and a venturi tray; and counter current contact devices using a turbo-grid tray, a dual flow tray, a ripple tray, a kittel tray, gauze type, sheet type, and grid type structured packings and random packings may be cited.

In this invention, it is advisable to supply the distillate 71 from the distillation column 70 which will be specifically described herein below and the residual mother liquid from the crystallizing device 50 which will be specifically described herein below (which will be referred to hereinafter as "circulating liquid") to the intermediate stage of the absorption column 30 during the absorption of acrylic acid by the contact of the acrylic acid-containing gas 25 with the absorbing aqueous solution 33. The circulating liquid contains acetic acid and may be used as an acetic acid-containing solution. In this invention, the term "different from the column top" refers to the range of number of theoretical plates of 2–100 on the assumption that the number of theoretical plate 1 denotes the column top of the absorption column and the number of theoretical plate 100 denotes the column bottom thereof. The acrylic acid is absorbed by the absorbing aqueous solution 33 falling from the column top. It has been found that when the acetic acid is introduced from a position different from the column top of the absorption column during this absorption, the absorption ratio of acrylic acid is enhanced. Though the mechanism for this enhancement remains yet to be clarified, it may be logically explained by a supposition that the introduction of acetic acid at a certain position of the absorption column 30 results in forming an acetic gas layer in the neighborhood of the position of the supply of acetic acid, changing the gas distribution in the absorption column so as to form a gas layer of a lower boiling substance above the acetic acid gas layer, and a gas layer of a higher boiling substance below it, and consequently moving the acrylic acid toward the column bottom side. Particularly, it is commendable to introduce the acetic acid-containing solution via the intermediate stage of the absorption column such as in the range of number of theoretical plates 2–100, preferably 25–100, and particularly 50–100. At the column top, the formation of the acetic acid gas layer produces no marked effect in enhancing the absorption efficiency of acrylic acid but rather decreases the absorption efficiency of acrylic acid, with the result that the acrylic acid concentration on the column bottom side is decreased and the acrylic acid-containing solution of high concentration cannot be obtained.

Advisably, the acetic acid concentration in the circulating liquid mentioned above properly not less than 2 wt. % and preferably falls in the range of 2–20 wt. % and particularly in the range of 3–15 wt. %. If this concentration falls short of 2 wt. %, the shortage will result in lowering the effect of the variation of the gas phase distribution in the absorption column mentioned above.

The amount of the circulating liquid is adjusted so that the amount of acetic acid to be introduced reaches a mass flow rate 0.005–0.2 times, preferably 0.008–0.15 times, and particularly 0.01–0.1 times the mass flow rate of acrylic acid contained in the acrylic acid-containing gas. When necessary, acetic acid may be added anew. If the amount mentioned above falls short of 0.005 times, the shortage will result in dulling the effect of enhancing the absorption efficiency of acrylic acid. Conversely, if the amount exceeds 0.2 times, the excess will result in widely increasing the acetic acid concentration in the absorbing liquid and consequently rendering the acquisition of acrylic acid-containing solution of high concentration difficult.

As the absorbing aqueous solution 33 to be used in this invention, a wide variety of aqueous solutions which are capable of absorbing acrylic acid are available. The condensate resulting from cooling the recycle gas may be used as the absorbing aqueous solution. Since the condensate often contains acrylic acid, it is preferred to be reused as the absorbing aqueous solution. The temperature of the absorbing aqueous solution at the time of introduction falls in the range of 0–50° C. and preferably in the range of 10–40° C.

The flow rate ratio to mass of the absorbing water (which excludes the condensate from the recycle gas and corresponds to the absorbing water 33' shown in FIG. 1) to the acrylic acid-containing gas may be properly selected to suit the target acrylic acid concentration. The absorption of acrylic acid is effected by counter current contact using a mass flow rate of the absorbing water of 0.1–1.5 times, preferably 0.1–1.0 times, and particularly 0.15–0.8 times to the mass flow rate of acrylic acid contained in the acrylic acid-containing gas. If the mass flow rate ratio falls short of the level of 0.1 times, the shortage will possibly induce an extreme decrease of the efficiency of the acrylic acid absorption column. Conversely, if it exceeds the level of 1.5 times, the excess will render the acquisition of an acrylic acid-containing solution of high concentration difficult. Incidentally, the absorbing water may contain therein for the purpose of preventing such polymerizing substances as acrylic acid from succumbing to polymerization one or more compounds selected from the group consisting of N-oxyl compounds, phenol compounds, manganese salts such as manganese acetate, copper salts of dialkyl-dithiocarbamic acid such as copper dibutylthiocarbamate, nitroso compounds, amine compounds, and phenothiazine which are cited as in JP-A-2001-348360, JP-A-2001-348358, and JP-A-2001-348359.

The acrylic acid absorption column is generally operated above normal pressure. In this invention, the column top pressure (gauge pressure) is set in the range of 0–0.4 MPa, preferably in the range of 0–0.1 MPa, and particularly in the range of 0–0.03 MPa. If this pressure falls short of 0 MPa (gauge pressure), the shortage will necessitate a pressure decreasing device and consequently add to the cost of equipment and the cost of utilities. Conversely, if the pressure exceeds 0.4 MPa (gauge pressure), the excess will possibly require the temperature of the absorption column to be elevated considerably for the purpose of discharging a low boiling substance from the column top and consequently degrade the absorption efficiency. The column top temperature falls generally in the range of 30–85° C. and particularly in the range of 40–80° C. In this invention, the acrylic acid-containing solution 35 comprising 80–98 wt. % of acrylic acid, 1–19 wt. % of water, and 1–10 wt. % of impurities (such as acids like acetic acid, maleic acid, and propionic acid, furfural, and aldehydes like formaldehyde) is obtained under the conditions of absorption mentioned above.

The method for cooling the recycle gas does not need to be particularly restricted. It is only required to resort to a device which is capable of condensing the condensable substances contained in the recycle gas. As concrete examples of the device answering the description, the shell-and-tube type heat exchanger, fin tube type heat exchanger, air cooled heat exchanger, double pipe heat exchanger, coil type heat exchanger, direct contact type heat exchanger, and plate type heat exchanger may be cited. Since the condensate more often than not contains such polymerizable substances as acrylic acid, however, the method of cooling which resorts to the combination of the cooling column 36 and such a cooling device 39 as illustrated in FIG. 1 is commendable in respect that it permits easy supply of a polymerization inhibitor.

The cooling temperature of the recycle gas does not need to be particularly restricted. When the recycle gas is cooled condensation, the concentration of the water component therein falls in the range of 0–10 vol %, preferably in the range of 0–7 vol %, and particularly in the range of 0–6 vol % and further the concentration of the total acid falls in the range of 0–0.2 vol %, preferably in the range of 0–0.1 vol % based on the total amount of the raw material gas supplied to the reactor. When air is used as the molecular oxygen-containing gas, the air contains a water component. The amount of the water component which exists after the recycle gas is cooled is computed from the amount of the air supplied, the aforementioned preferred concentration of the water component in the raw material gas and the amount of the raw material gas supplied. The cooling of Recycle gas is carried out till the concentration the water component reach the value found by the computation. In this invention, the recycle gas is cooled to a temperature which is 1–50° C., preferably 2–40° C., and particularly preferably 3–30° C. lower than the temperature of the waste gas.

Consequently, the bottom liquid of the absorption column having an extremely high acrylic acid concentration is not less than 80 wt. % can be obtained.

(2) Separation of Acrolein

The acrylic acid-containing solution 35 possibly contains acrolein which is the raw material of acrylic acid. The removal of this contained acrolein may be accomplished by supplying the solution to the acrolein separation column 31 and giving it a treatment for removal of acrolein.

The separation column does not need to be particularly restricted but is only required to be capable of separating acrolein. A packed column, a plate column (tray column), etc. are available. As regards the conditions of the separation column, the method of separation may be properly selected from among distillation, stripping, and the like, depending on the concentration of the contained acrylic acid and the concentration of acrolein. In the case of distillation, it is advisable to set the column top pressure (absolute pressure) in the range of 20–800 hPa, preferably in the range of 40–600 hPa, and particularly in the range of 60–400 hPa. If this pressure falls short of 20 hPa (absolute pressure), the shortage will be at a disadvantage in requiring the column, condenser, and vacuum device to be enlarged and entailing an increased cost of equipment. Conversely, if this pressure exceeds 800 hPa (absolute pressure), the excess will be at a disadvantage in heightening the temperature in the separation column and exalting the possibility of polymerization. The column top temperature falls generally in the range of 30–100° C. and particularly in the range of 40–80° C. The column bottom temperature falls generally in the range of 40–110° C. and particularly in the range of 50–90° C. Incidentally, in the case of stripping, the separation of acrolein may be effected by any of the hitherto known methods. By the separation performed under these conditions, it is made possible to decrease the amount of acrolein and obtain an acrylic acid-containing solution having an acrylic acid concentration of not less than 80 wt. %.

(3) Step of Crystallization of Acrylic Acid-Containing Solution.

This invention obtains a purified acryl acid 60 by supplying the acrylic acid-containing solution 35 or 35' to the crystallizing device 50.

The method of crystallization to be used does not need to be particularly restricted. The crystallization may be effected either continuously or batchwise and may be performed in one stage or in two or more stages. As a concrete example of the continuous crystallizing device, backmixing column crystallizer (BMC) (made by Nippon Steel Chemical Co., Ltd.) as a column type crystallizer having a crystallizing part, a solid-liquid separating part, and a crystal purifying part integrated may be cited. A cooling disk crystallizer (CDC) (made by Gouda Company of Netherlands), for example, is used as the crystallizing part, a belt filter or a centrifugal separator, for example, is used as the solid-liquid separating part, and Kureha Crystal Purifier (KCP) (made by Kureha TechnoEngineering Co. Ltd.), for example, is used as the crystal purifying part respectively in the continuous crystallizing device.

As a concrete example of the crystallizing device 50, what is formed by combining a crystallizing device, a solid-liquid separating device, and a crystal purifying device may be cited. One advantageous mode of embodying this invention consists in a method which uses a continuous crystallizing apparatus. As the crystallizing part, a system having arrayed two crystallizers (CDC) of the construction illustrated on pages 77–78 of the July, 2001 issue of "Chemical Devices" may be used. The inside of the crystallizers (1) and (2), namely, horizontal crystallizing tanks, is partitioned with several cooling plates whose lower parts have the opening of passages. They are operated to effect cooling and crystallization through these cooling plates. A stirring shaft piercing the centers of the cooling plates is provided with wipers for renewing the cooling surfaces and the stirring vanes. The liquid supplied through a raw material liquid supply port is sequentially moved by the stirring shaft through the passages below the cooling plates toward the other terminal. When an aqueous acrylic acid solution is supplied to the crystallizer (1), for example, it is crystallized in this crystallizer and the resultant crystals are separated by a solid-liquid separating part, namely, a belt filter, into crystals and a mother liquid. Subsequently, the crystal mother liquid is supplied to the crystallizer (2) so as to have acrylic acid crystallized and then separated by a belt filter into crystals and a mother liquid. Then, the crystals obtained by these crystallizers (1) and (2) are introduced into the crystal purifying part. Properly the total amount of crystallization of acrylic acid to be attained jointly by the crystallizers (1) and (2) is adjusted to be not less than 20 wt. % and preferably fall in the range of 30–90 wt. %, particularly in the range of 40–90 wt. %. As a result, the acetic acid concentration in the residual mother liquid is enabled to exceed 2 wt. %. As the crystal purifying part, a crystal purifying device (KCP) inserted on pages 76–77 of the July, 2001 issue of "Chemical Devices" and disclosed in JP-B-1972-40621 may be used. As a concrete example of this device, a metallic cylinder which is provided at the center thereof with a screw conveyor, in the upper part thereof with a melting device for fusing crystals and an output port for the product resulting from the melting, in the lower part thereof with an output port for the residual liquid, and in the lower column side part thereof with a supply port for crystals may be cited. The crystals are conveyed by the screw conveyor to the upper part of the purifying column and melted by the melting device. The resultant solution is withdrawn through the product output port and part of the withdrawn solution is made to fall from the upper part of the purifying column. Owing to the fall of the solution, the crystals delivered by the screw conveyor are cleaned and caused to sweat. The solution falling from the upper part is withdrawn via the residue output port below. The amount of the falling solution may be properly selected to suit the target purity of acrylic acid. Commendably it falls in the range of 1–60 wt. %, preferably in the range of 2–40 wt. %, and particularly in the range of 5–35 wt. % of the amount of the melting solution. If this amount falls short of 1 wt. %, the shortage will result in lowering the effect of washing and sweating of crystals. Conversely, it is exceeds 60 wt. %, the excess will result in preventing the effect of washing and sweating from being enhanced and possibly rendering the operation of the crystal purifying column difficult. The withdrawn residue may be circulated to the crystallizing device and/or the residual mother liquid of crystallization mentioned above or partly withdrawn from the system.

Another advantageous mode of embodying this invention consists in a method which uses a batchwise crystallizing device. As the device of this sort, a layer crystallizing device (dynamic crystallizing device) made by Sulzer Chemtech Company of Switzerland and a static crystallizing device made by BEFS Prokem Company of France are available.

In the batchwise crystallization, the number of crystallizing steps to be required depends on the degree of purification aimed at. In this invention, to produce acrylic acid of high purity, it is commendable to perform the step of purification (step of dynamic crystallization) up to 1–6 repetitions, preferably 2–5 repetitions, and more preferably 2–4 repetitions and the step of stripping (Step of dynamic crystallization and/or step of static crystallization) up to 0–5 repetitions and preferably 0–3 repetitions. The residue which is withdrawn may be partly discarded to the out side of system.

The step of crystallizing purification may be preceded by preliminary purification. The preliminary purification is executed by crystallization. The step of preliminary purification and the subsequent step of purification, therefore, may be regarded as a series of steps of crystallization. The preliminary purification may utilize a device for preliminary purification which is formed by combining a crystallizing device and a solid-liquid separating device, for example. The CDC crystallizer, the tank crystallizer, etc. are available as the crystallizing device and the belt filer, the centrifugal separator, etc. are available as the solid-liquid separating device.

One advantageous mode of embodying this invention and embracing the preliminary purification has a device for preliminary purification comprising a tank crystallizer and a centrifugal separator. The tank crystallizer is formed of two columns which are disposed in series connection and are each furnished with a stirrer and provided with a surface formed of a double-wall jacket controlled at a fixed temperature with a thermostat. First, the first crystallizing tank receives supply of an aqueous acrylic acid solution and crystallizes the contained acrylic acid, separates the treated solution into crystals and a mother liquid by means of the centrifugal separator, and washes the crystals with a melt. Then, the mother liquid and the washing liquid consequently obtained are supplied to the second crystallizing tank so as to have the contained acrylic acid crystallized and separated into crystals and the mother liquid with the centrifugal separator. The isolated crystals are washed with the melt. The total amount of crystallization of acrylic acid attained jointly by the first crystallizing tank and the second crystallizing tank properly is not less than 20 wt. % and preferably falls in the range of 30–90 wt. % and particularly 40–90 wt. %. As a result, the acetic acid concentration in the residual mother liquid can be made to surpass 2 wt. %. The crystals consequently obtained are fused and the acrylic acid-containing solution which has undergone the preliminary purification is further purified.

The purification constitutes a method of multistage fractional crystallization, for example. This crystallization can be performed by a step of dynamic crystallization using a dynamic crystallizing device provided with a tubular crystallizing device provided with a temperature controlling mechanism for performing crystallization, sweating, and melting, a tank for recovering the mother liquid occurring after the sweating, and a circulating pump for supplying acrylic acid to the crystallizing device and adapted to transfer acrylic acid by means of a circulating pump from a storage vessel disposed in the lower part of the crystallizing device to the upper part of the tube of the crystallizing device or by the combination of a step of dynamic crystallization and a step of static crystallization using a tubular crystallizing device provided with a temperature controlling mechanism for performing crystallization, sweating, and melting and furnished in the lower part thereof with an drawing-out valve and using a tank for recovering the mother liquid occurring after the sweating with a step of static crystallization.

A crude acrylic acid-containing solution is introduced as a liquid phase into the crystallizer and then a solid phase different in composition from the introduced liquid phase is solidified in the cooling surface. When a portion in the range of 40–90 wt. %, preferably 50–80 wt. %, of the used acrylic acid is solidified, the remainder of the liquid phase is immediately separated and removed. This separation and removal is effected by scooping the residual phase with a pump (step of dynamic crystallization) or causing it to flow out (step of static crystallization). Subsequently, a step of washing the crystal layer or so-called sweating, namely partial melting-off of the region of impure crystals may be further carried out.

When the dynamic crystallization and static crystallization are carried out in a multistage step, they can be executed advantageously by the principle of counter current. The substances which have been crystallized in the component steps are separated from the residual mother liquid and these crystallized substances are supplied to the next steps involving still higher levels of purity. Meanwhile, the residues of crystallization are supplied to the subsequent steps involving still lower levels of purity.

Generally, all the steps in which acids of higher purity than the supplied crude acid-containing solutions are known as purifying steps and all the other steps are known as stripping steps. The stripping steps are performed with the object of recovering acrylic acid in the mother liquids from the purifying steps. The dynamic crystallization incurs difficulty which increases in proportion as the purity of acrylic acid decreases. In contrast, the static crystallization proceeds easily as compared with the dynamic crystallization even when the purity of acrylic acid is lowered. For the purpose of exalting the recovery ratio of acrylic acid, the final mother liquid in the dynamic crystallization is further crystallized by the static crystallization.

The number of steps of crystallization which are required depends on the degree of purity which is expected. For the purpose of obtaining acrylic acid of high purity, it is proper to perform the purifying step (step of dynamic crystallization) up to 1–5, preferably 2–3 repetitions, the stripping step (step of dynamic crystallization) up to 1–5, preferably 1–4 repetitions, and the stripping step (step of static crystallization) up to 1–5, preferably 1–3 repetitions.

The residue withdrawn from the final round of the step of static crystallization may be circulated to the residual mother liquid of crystallization occurring in the preliminary purification mentioned above or may be withdrawn to the out side of system.

(4) Distillation of Acrylic Acid-Containing Solution

The residual mother liquid from the crystallizing device 50 contains such low boiling substances as acetic acid and water and such high boiling substances as acrylic acid dimer and a polymerization inhibitor besides acrylic acid of high concentration. This invention, for the purpose of effectively utilizing the residual mother liquid, contemplates supplying at least part of the residual mother liquid to the distillation column 70 so as to withdraw high boiling substances via the bottom of the column and obtain low boiling substances and acrylic acid in the form of distillate via the top of the column. As the distillation column 70 which is used for this purpose, a packed column, a plate column (tray column), etc. are available.

The distillation is executed under such conditions as induce expulsion of such low boiling substances as water and acetic acid as well as acrylic acid by distillation. These conditions may be properly selected, depending on the acrylic acid concentration, water concentration, and acetic acid concentration in the residual mother liquid to be introduced. Generally, it is proper to select the column top pressure (absolute pressure) in the range of 10–400 hPa, preferably 15–300 hPa, and particularly 20–200 hPa. If this pressure falls short of 10 hPa (absolute pressure), the shortage will be at a disadvantage in requiring the column, condenser, and vacuum device to be enlarged and consequently adding to the cost of equipment. Conversely, if the pressure exceeds 400 hPa (absolute pressure), the excess will be at a disadvantage in heightening the temperature in the distillation column 70 and consequently adding to the possibility of polymerization. The column top temperature falls generally in the range of 30–70° C. and particularly in the range of 40–60° C. The bottom temperature in the column falls 50–140° C., particularly 60–120° C. Under these conditions of distillation, the distillate 71 having a higher acetic acid concentration than the acetic acid concentration in the residual mother liquid is obtained. The distillate 71 is circulated to the absorption column 30.

For the purpose of preventing such polymerizable substances as acrylic acid from succumbing to polymerization during the course of distillation, it is permissible to add a polymerization inhibitor to the reflux liquid. As the polymerization inhibitor for use in this case, various polymerization inhibitors suitable for addition to the absorbing aqueous solution enumerated above are available.

(5) Decomposition of Acrylic Acid Dimer

The bottom liquid of the distillation column 70 contains acrylic acid dimer. The decomposition of this acrylic acid dimer results in recovery of acrylic acid. An acrylic acid dimer decomposition devise does not need to be particularly restricted but is only required to be capable of decomposing acrylic acid dimer and recover acrylic acid consequently. For example, it may be capable of simultaneously executing decomposition of acrylic acid dimer and expulsion of acrylic acid by distillation (refer to JP-B-1986-35977 and JP-B-1986-36501). Preferably, it may resort to the use of a tray column which is provided with a thin-film vaporizer and a dimer decomposing tank (refer to JP-A-1999-12222).

The acrylic acid dimer decomposing device mentioned above may be used anew separately of the distillation column 70. Preferably, the decomposition may be executed in a form having a dimer decomposing tank annexed to the distillation column 70 which is provided with a thin layer evaporator.

Specifically, the bottom liquid of the distillation column 70 (the bottom liquid of the thin layer evaporator 73) are introduced into the dimer decomposing tank 75 so as to decompose the contained acrylic acid dimer. The dimer decomposing tank 75 decomposes the acrylic acid dimer at a temperature in the range of 120–220° C. with a hold up time (capacity of dimer decomposing tank/amount of waste oil) generally set in the range of 0.1–60 hours, though variable with the temperature of thermal decomposition. After the acrylic acid dimer is decomposed into acrylic acid, the acrylic acid can be recovered via the top of the distillation column 70 by circulating the acrylic acid resulting from the decomposition to the thin layer evaporator.

When the acrylic acid recovering column which is provided with the thin layer evaporator and a dimer decomposing tank is used separately of the distillation column 70, the recovered acrylic acid which is obtained via the top of the acrylic acid recovering column may be circulated to the distillation column 70 and/or the absorption column 30.

To the dimer decomposing tank, a catalyst for decomposition such as an alkali metal salt, an alkaline earth metal salt, or an N-oxy compound mentioned in JP-A-2003-89672 may be added during the course of the decomposition of acrylic acid dimer. When the N-oxy compound mentioned above is used as a polymerization inhibitor in the step of absorption or the step of distillation, it additionally functions as a catalyst for the decomposition of acrylic acid dimer.

EXAMPLES

Now, this invention will be described more specifically below with reference to working examples thereof.

Example of Production of Catalyst

A molybdenum-bismuth type catalyst was prepared by following the procedure described in JP-A-2000-325795. It was labeled as "Catalyst (I)." A molybdenum-vanadium type catalyst was prepared by following the procedure described in JP-A-1996-206504. It was labeled as "Catalyst II."

Example 1

Acrylic acid was produced by using an apparatus illustrated in FIG. 1.

A reactor furnished on the outer periphery thereof with a jacket for circulating a heat medium, containing therein reaction tubes 25 mm in inside diameter and 7,000 mm in length, and provided at a position of 3,500 mm from the lower part of the jacket with a perforated tube sheet dividing the heat medium jacket into two halves, an upper one and a lower one, was used. The lower part (the first reaction zone) and the upper part (the second reaction zone) of the reactor had their temperatures controlled by circulation of their respective heat media. The reactor was packed with (1) ceramic balls having an average diameter of 5 mm, (2) a mixture of catalyst (I) and ceramic balls of an average diameter of 5 mm at a volume ratio of 70:30, (3) catalyst (I), (4) raschig rings made of stainless steel and measuring 5 mm in outside diameter, 4.5 mm in inside diameter, and 6 mm in length, (5) a mixture of catalyst (II) and ceramic balls of an average diameter of 5 mm at a volume ratio of 75:25, and (6) catalyst (II) placed sequentially from the lower part toward the upper part of the reactor in respective bed lengths of 250 mm, 700 mm, 2,300 mm, 500 mm, 600 mm, and 1,900 mm.

To the first reaction zone of the reactor, propylene, air (the concentration of water component 2 wt. %), and part of the discharged gas (recycle gas) from the absorption column were circulated to supply 8.0 vol % of propylene, 14.4 vol % of $O_2$, and 2.0 vol % of $H_2O$ (the remainder comprising $N_2$, propane, $CO_x$, acrylic acid, and acetic acid) with the respective flow rates and the cooling temperature of the recycle gas so adjusted as to set the space velocity in the first reaction zone at 1,250 $hr^{-1}$ (STP).

The heat medium temperatures of the first reaction zone and the second reaction zone were so adjusted as to set the degree of conversion of propylene at 97±0.5 mol % and the yield of acrolein at 1±0.5 mol % under the outlet pressure, 0.15 MPa (absolute pressure), of the second reaction zone. Consequently, an acrylic acid-containing gas containing 16.62 wt. % of acrylic acid was obtained at a rate of 18.77 kg/hour.

Then, the acrylic acid-containing gas consequently obtained was cooled to 200° C. with a precooler and led to an acrylic acid absorption column so as to collect an acrylic acid-containing solution.

The absorption column mentioned above was a packed column filled with structured packings, possessing a number of theoretical plate of 21 found by computation, provided in the column bottom part thereof with a supply port for acrylic acid-containing gas and an outlet port for the absorbing liquid, in the column top part thereof with an inlet port for the absorbing aqueous solution and an outlet port for the gas, and in the column side part thereof ($19^{th}$ theoretical plate) with a supply tube for the column top liquid from the distillation column, and further furnished with a cooling device for cooling part of the gas discharged via the column top part.

As the absorbing water, water containing hydroquinone in an amount corresponding to 200 wt. ppm relative to the amount of acrylic acid in the acrylic acid-containing gas introduced to the absorption column was supplied at a rate of 1.01 kg/hour.

The absorption was performed under the conditions of 66.9° C. of column top temperature of the acrylic acid absorption column, 0.11 MPa (absolute pressure) of column top pressure, 40.6° C. of cooling temperature of the recycle gas, and 29.0% of the rate of recycling. The condensate obtained by cooling the recycle gas was wholly circulated to the absorption column.

Via the column side part, the circulating liquid formed of the distillate of distillation column and the residual mother liquid of the crystallizing device and having a composition of 74.8 wt. % of acrylic acid, 8.6 wt. % of water, 5.1 wt. % of acetic acid, 2.1 wt. % of maleic acid, 0.2 wt. % of furfural, 0.8 wt. % of benzaldehyde, 0.2 wt. % of formaldehyde, 4.2 wt. % of acrylic acid dimer, and 4.0 wt. % of other impurities supplied at a rate of 1.90 kg/hour.

The absorption efficiency of acrylic acid in the absorption column at this time was 98.22%.

The acrylic acid-containing solution was supplied to the upper part of a packed column measuring 100 mm in inside diameter and 5 m in packed bed height so as to separate acrolein by distillation induced by keeping the column top pressure at 265 hPa (absolute pressure) and the column bottom temperature at 70° C. by heating. As a result, an aqueous acrylic acid solution containing 89.0 wt. % of acrylic acid, 3.2 wt. % of water, 1.9 wt. % of acetic acid, 1.1 wt. % of maleic acid, 0.07 wt. % of furfural, 0.3 wt. % of benzaldehyde, 0.06 wt. % of formaldehyde, 2.3 wt. % of acrylic acid dimer, and 2.07 wt. % of other impurities was obtained at a rate of 5.10 kg/hour. The gas obtained from the column top part was supplied to the lower part of the acrylic acid absorption column.

Then, this acrylic acid-containing solution was supplied to a crystallizing device and crystallized therein. The crystallizing device was formed of two crystallizers disposed in series connection as described on pages 77–78 of the July, 2001 issue of "Chemical Devices." The crystallizers were each formed of a horizontal crystallizing tank having the interior thereof partitioned with several cooling plates (the lower parts thereof were separated with a gap serving as a passage). The cooling and the crystallization were executed through these cooling plates. A stirring shaft piercing the centers of the cooling plates was provided with wipers serving to renew cooling surfaces and stirring vanes. The liquid supplied through a raw material liquid supply port at one terminal was sequentially moved by the stirring shaft through the passage underlying the cooling plates toward the other terminal. When the aqueous acrylic acid solution was supplied to the first crystallizing device, this device crystallized acrylic acid, caused the belt filter to separate the solution into crystals and a mother liquid, and supplied the mother liquid consequently obtained to the second crystallizer. The second crystallizer crystallized acrylic acid and caused the belt filter to separate the solution into crystals and a mother liquid. The crystallizer was operated with the temperature of the cooling plates of the first crystallizing device adjusted to 0° C., the temperature of the cooling plates of the second crystallizing device adjusted to –7° C., and the total amount of crystallization of acrylic acid attained jointly by the first and the second crystallizing device at 68 wt. % of the amount of acrylic acid supplied to the first crystallizing device.

Then, the crystals obtained by the first and the second crystallizing device were supplied to the crystal purifying device.

This device conformed with the crystallizing device described on pages 76–77, July 2001 issue of "Chemical Devices" and in JP-B-1972-40621. Specifically, it was a metallic cylinder which was provided along the center thereof with a screw conveyor, in the upper part thereof with a fusing device for fusing crystals and an outlet port for the finished product resulting from the melting, in the lower part thereof with an outlet port for the residual liquid, and in the lower side part thereof with a supply port for crystals. The crystals were conveyed to the upper part of the purifying device by the screw conveyor and fused by the fusing device. The resultant Melt was withdrawn through a product output port and 10 wt. % of the Melt was left fall from the upper part of the device. The fall of the Melt enabled the crystals delivered by the screw conveyor to be washed and exuded. The liquid falling from the upper part was withdrawn through the residue output port below.

Thus, acrylic acid having purity of 99.94 wt. % was obtained at a rate of 3.12 kg/hour. At this time, it contained 40 wt. ppm of water, 515 wt. ppm of acetic acid, 4 wt. ppm of maleic acid, 0.1 wt. ppm of furfural, 0.5 wt. ppm of benzaldehyde, 0.0 wt. ppm of formaldehyde, and 40 wt. ppm of acrylic acid dimer.

The yield of purification of acrylic acid was 99.9%.

Thirty % of the residual mother liquid obtained from the second crystallizing device and the residue withdrawn from the crystal purifying device was supplied to the intermediate part of the distillation column of the acrylic acid dimmer decomposing device. The acrylic acid dimer decomposing device had a structure resulting from combining a distillation column fitted with 15 dual flow tray, a dimer decomposing tank for decomposing the acrylic acid dimer, and a thin layer evaporator. It was operated by effecting thermal decomposition under the conditions of 145° C. of the internal temperature of the dimer decomposing tank and 4 hours of the hold up time, controlling the thin layer evaporator so as to set the column bottom temperature at 85° C., and a reflux ratio of 0.1 at a column top pressure of 33 hPa added 4H-TEMPO (4-hydroxy-2,2,6,6-tetramethyl piperidinoxyl) as a stabilizer from the reflux liquid to the acrylic acid supplied to the distillation column in an amount corresponding to 200 ppm relative to the acrylic acid supplied to the distillation column. To the dimer decomposing tank, an aqueous 20 wt. % sodium hydroxide solution was supplied as a catalyst for the decomposition of acrylic acid dimer in an amount of 0.04 wt. % (as reduced to NaOH) relative to the residual mother liquid to be supplied.

From the column top part, acrylic acid containing 82.9 wt. % of acrylic acid, 9.6 wt. % of water, and 5.7 wt. % of acetic acid was recovered at a rate of 0.51 kg/hour. The recovered acrylic acid was circulated together with the residual mother liquid of the second crystallizing device and the residue of the crystal purifying device to the column side part of the absorption column. The circulating liquid had the following composition: 74.8 wt. % of acrylic acid, 8.6 wt. % of water, 5.1 wt. % of acetic acid, 2.1 wt. % of maleic acid, 0.2 wt. % of furfural, 0.8 wt. % of benzaldehyde, 0.2 wt. % of formaldehyde, 4.2 wt. % of acrylic acid dimer, and 4.0 wt. % of other impurities.

Example 2

Figure 2:
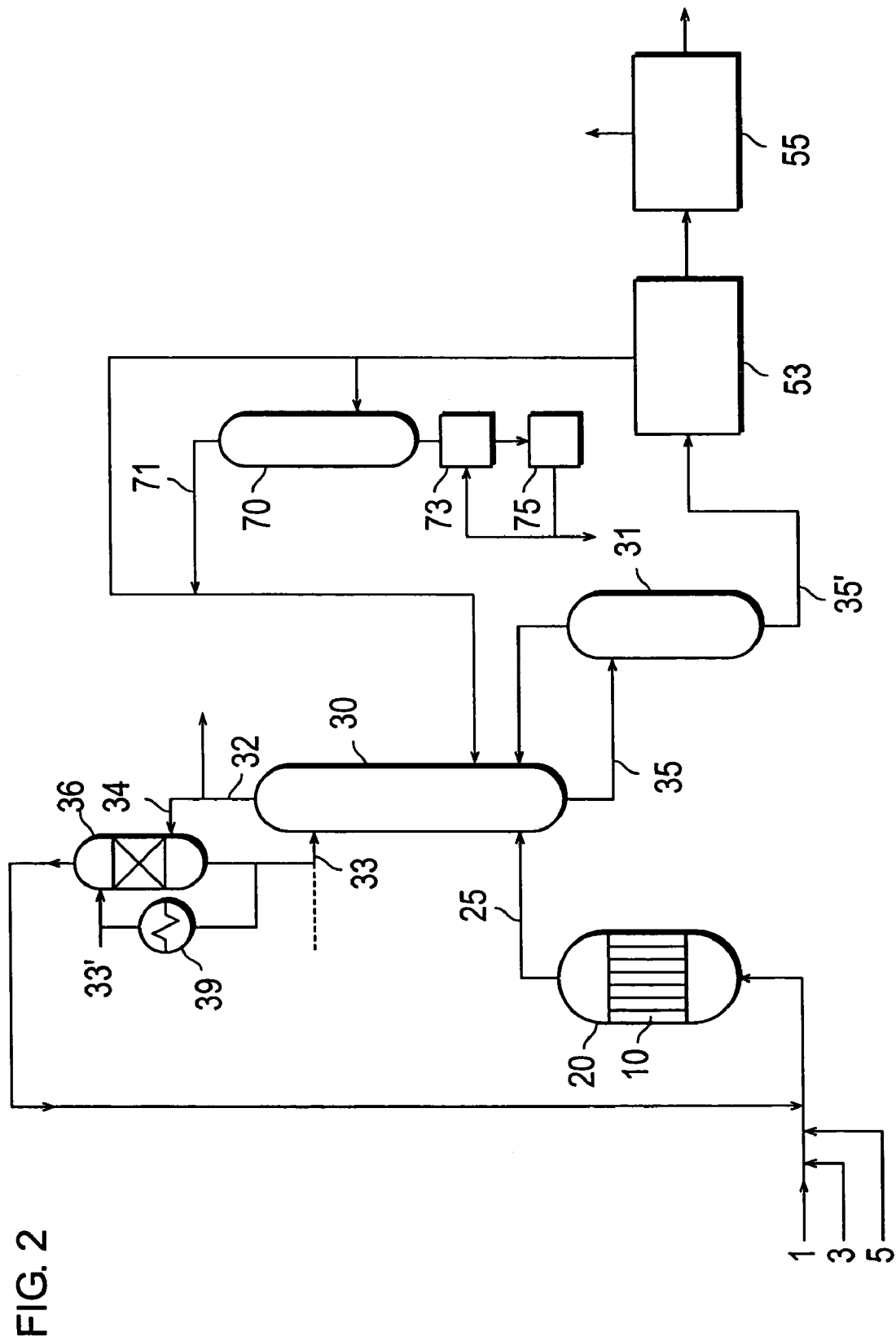
FIG. 2 is a process diagram of the production of acrylic acid which is used in Example 2 of this invention.

Acrylic acid was produced by using an apparatus illustrated in FIG. 2.

The production was performed by following the procedure of Example 1 while supplying as the circulating liquid composed of the distillate of distillation column and the residual mother liquid of the crystallizing device and having a composition of 77.5 wt. % of acrylic acid, 8.5 wt. % of water, 4.8 wt. % of acetic acid, 2.1 wt. % of maleic acid, 0.2 wt. % of furfural, 0.6 wt. % of benzaldehyde, 0.2 wt. % of formaldehyde, 2.5 wt. % of acrylic acid dimer, and 3.6 wt. % of other impurities from the column side part. Consequently, an aqueous acrylic acid solution containing 89.9 wt. % of acrylic acid, 3.2 wt. % of water, 1.9 wt. % of acetic acid, 1.1 wt. % of maleic acid, 0.06 wt. % of furfural, 0.2 wt. % of benzaldehyde, 0.06 wt. % of formaldehyde, 1.6 wt. % of acrylic acid dimer, and 1.98 wt. % of other impurities was obtained from the column bottom part of the packed column at a rate of 5.05 kg/hour. The gas obtained from the column top part was supplied to the lower part of the acrylic acid absorption column.

The absorption efficiency of acrylic acid in the absorption column at this time was 98.21%.

Then, this aqueous acrylic acid solution was supplied to the device of preliminary purification formed of a crystallizing tank and a centrifugal separator so as to undergo crystallization. The crystallizing tank was formed of two vessel disposed in series connection. These vessels were each provided with a stirrer and furnished on the surface thereof with a double-wall jacket. This jacket was controlled so as to be set at a certain fixed temperature with a thermostat. First, an aqueous acrylic acid solution was supplied to the first crystallizing tank. This vessel crystallized acrylic acid in the solution, caused the centrifugal separator to separate the solution into crystals and a mother liquid, and washed the crystals with a Melt. The mother liquid and the washing liquid consequently obtained were supplied to the second crystallizing tank. This vessel crystallized acrylic acid in the solution, caused the centrifugal separator to separate the solution into crystals and a mother liquid, and washed the crystals with the Melt. The jacket temperature of the first crystallizing tank was −5° C., the jacket temperature of the second crystallizing tank was −14° C., and the washing liquid was supplied at 0.16 kg/hour. From the first and the second crystallizing tank, acrylic acid containing 98.9 wt. % of acrylic acid, 0.2 wt. % of water, 0.3 wt. % of acetic acid, 0.3 wt. % of maleic acid, 0.003 wt. % of furfural, 0.01 wt. % of benzaldehyde, 0.002 wt. % of formaldehyde, and 0.4 wt. % of acrylic acid dimer was obtained at a rate of 3.15 kg/hour.

Thirty % of the residual mother liquid obtained from the crystallizing tank 2 was supplied to the intermediate part of the distillation column of the acrylic acid dimmer decomposing device. The acrylic acid dimer decomposing device equaled that used in Example 1 and was operated under the same conditions as in Example 1.

From the column top part, a distillate containing 84.0 wt. % of acrylic acid, 9.3 wt. % of water, and 5.3 wt. % of acetic acid was recovered at a rate of 0.50 kg/hour. The recovered distillate was circulated together with the remaining residual mother liquid to the column side part of the absorption column. The circulating liquid had the following composition: 77.5 wt. % of acrylic acid, 8.5 wt. % of water, 4.8 wt. % of acetic acid, 2.1 wt. % of maleic acid, 0.2 wt. % of furfural, 0.6 wt. % of benzaldehyde, 0.2 wt. % of formaldehyde, 2.5 wt. % of acrylic acid dimer, and 3.6 wt. % of other impurities.

Then, the acrylic acid obtained from the crystallizing tank was supplied to another crystallizing device and purified therein by performing a step of dynamic crystallization up to 2 repetitions. Further, the residue of crystallization from this step of purification was treated by performing a step of dynamic crystallization up to three repetitions and a step of static crystallization up to two repetitions.

The dynamic crystallization was performed in a crystal purifying device conforming to the crystallizing device disclosed in JP-B-1978-41637. Specifically, this device was a metallic cylinder provided in the lower part thereof with a storage vessel, measuring 6 m in length and 70 mm in inside diameter, and adapted to transfer the liquid in the storage vessel to the upper part of the cylinder with a circulating pump and allow the liquid to flow down the inner wall surface of the cylinder in the form of a falling film. The cylinder was furnished on the surface thereof with a double-wall jacket which was controlled to be retained at a certain fixed temperature with a thermostat. One round of the dynamic crystallization was performed by the following procedure.

1. Crystallization: Acrylic acid was supplied to the storage vessel and caused to fall down the wall surface of the cylinder in the form of a falling film by the circulating pump so as to lower the temperature of the jacket to e level below the solidifying point and induce deposition of crystals of about 60–80 wt. % of the acrylic acid crystals on the wall surface.

2. Sweating: The circulating pump was stopped and the temperature of the jacket was elevated to the neighborhood of the solidifying point to induce sweating of about 2–5 wt. % of the crystals. The residual Melt after the sweating was scooped out with the pump.

3. Melting: The temperature of the jacket was elevated to a level above the solidifying point to induce melting of the crystals. The resultant Melt was scooped out with the pump.

In the operation described above, the temperature and the solidifying point were dependent on the relevant steps.

The static crystallization was performed in a tube provided in the lower part thereof with a drawing-out valve, measuring 90 mm in inside diameter and 1 m in length, and furnished on the surface thereof with a double-wall jacket. This jacket was controlled to be retained at a certain fixed level with a thermostat. One round of the static crystallization was performed by the following procedure.

1. Crystallization: Acrylic acid was supplied into the tube and about 60–80 wt. % thereof was crystallized with the temperature of the jacket lowered to a level below the solidifying point.

2. Sweating: The residual mother liquid occurring after the crystallization was withdrawn through the lower part of the tube and about 15–25 wt. % thereof was caused to exude with the temperature of the jacket elevated to a level in the neighborhood of the solidifying point. After the sweating, the liquid formed by the sweating was withdrawn.

3. Melting: The temperature of the jacket was elevated to a level surpassing the solidifying point to induce melting of the crystals. The resultant Melt was withdrawn. Consequently, acrylic acid having such high purity as 99.95 wt. % was obtained at a rate of 3.07 kg/hour.

At this time, the acrylic acid contained 10 wt. ppm of water, 475 wt. ppm of acetic acid, 2 wt. ppm of maleic acid, 0.1 wt. ppm of furfural, 0.03 wt. ppm of benzaldehyde, 0.0 wt. ppm of formaldehyde, and 12 wt. ppm of acrylic acid dimer.

The yield of purification of acrylic acid was 98.5%.

Example 3

Acrylic acid was produced by using an apparatus illustrated in FIG. 1.

The operation of this production was performed by following the procedure of Example 1 while supplying a circulating liquid formed of the distillate of distillation column and the residual mother liquid of the crystallizing device and having a composition of 83.5 wt. % of acrylic acid, 6.7 wt. % of $H_2O$, 3.1 wt. % of acetic acid, 1.3 wt. % of maleic acid, 1.4 wt. % of furfural, 0.5 wt. % of benzaldehyde, 0.2 wt. % of formaldehyde, 2.6 wt. % of acrylic acid, and 0.7 wt. % of other impurities via the column side part. Consequently, an aqueous acrylic acid solution containing 90.2 wt. % of acrylic acid, 3.4 wt. % of water, 1.6 wt. % of acetic acid, 1.0 wt. % of maleic acid, 0.7 wt. % of furfural, 0.3 wt. % of benzaldehyde, 0.09 wt. % of formaldehyde, 2.4 wt. % of acrylic acid dimer, and 0.31 wt. % of other impurities was obtained from the column bottom part of a packed column at a rate of 6.36 kg/hour. The gas obtained from the top of the column was supplied to the lower part of the acrylic acid absorption column. At this time, the absorption efficiency of acrylic acid in the absorption column was 98.20%.

Then, this aqueous acrylic acid solution was purified by using the same dynamic crystallizing device as in Example 2 and performing the step of dynamic crystallization up to four repetitions.

Consequently, acrylic acid of such high purity as 99.94 wt. % was obtained at a rate of 3.09 kg/hour.

At this time, the acrylic acid contained 100 wt. ppm of water, 450 wt. ppm of acetic acid, 3 wt. ppm of maleic acid, 0.4 wt. ppm of furfural, 0.1 wt. ppm of benzaldehyde, 0.0 wt. ppm of formaldehyde, and 30 wt. ppm of acrylic acid dimer.

The yield of purification of acrylic acid was 99.0%.

Of the residual mother liquid obtained by the step of dynamic crystallization, 45% was supplied to the intermediate part of the distillation column of the acrylic acid dimmer decomposing device. The acrylic acid dimer decomposing and distillation column used herein equaled that of Example 1 and was operated under the same conditions as in Example 1.

Via the column top part, a distillate containing 86.4 wt. % of acrylic acid, 7.0 wt. % of water, and 3.2 wt. % of acetic acid was recovered at 1.42 kg/hr. The distillate was circulated together with the remaining residual mother liquid to the column side part of the absorption column. The circulated liquid had the following composition: 83.5 wt. % of acrylic acid, 6.7 wt. % of $H_2O$, 3.1 wt. % of acetic acid, 1.3 wt. % of maleic acid, 1.4 wt. % of furfural, 0.5 wt. % of benzaldehyde, 0.2 wt. % of formaldehyde, 2.6 wt. % of acrylic acid dimer, and 0.7 wt. % of other impurities.

Comparative Example 1

An operation was performed by following the procedure of Example 1 while omitting the circulation of the circulating liquid composed of the distillate of distillation column and the residual mother liquid of the crystallizing device to the absorption column. Consequently, an aqueous acrylic acid solution containing 90.0 wt. % of acrylic acid, 4.7 wt. % of water, 2.8 wt. % of acetic acid, 0.5 wt. % of maleic acid, 0.03 wt. % of furfural, 0.03 wt. % of benzaldehyde, 0.01 wt. % of formaldehyde, 1.0 wt. % of acrylic acid dimer, and 0.03 wt. % of other impurities was obtained via the tower bottom of the packed column at a rate of 3.46 kg/hour. The gas obtained via the column top part was supplied to the lower part of the acrylic acid absorption column. In Comparative Example 1, the absorption efficiency of acrylic acid was 97.90%.

The aqueous acrylic acid solution mentioned above and 80% of the mother liquid from the step of crystallization (having a composition of 43.6 wt. % of acrylic acid, 27.1 wt. % of water, 15.1 wt. % of acetic acid, 2.9 wt. % of maleic acid, 0.1 wt. % of furfural, 1.0 wt. % of benzaldehyde, 0.5 wt. % of formaldehyde, 5.8 wt. % of acrylic acid dimer, and 4.8 wt. % of other impurities) were purified by the same crystallizing device as in Example 1 at a rate of 2.40 kg/hour.

The acrylic acid consequently obtained had a purity of 99.71 wt. %. The yield of purification, therefore, was 91.7%.

RESULTS

Comparison of Example 1 and Comparative Example 1 reveals that when the supply of the circulating liquid to the absorption column was omitted, the absorption ratio of acrylic acid decreased from 98.21% to 97.90%. When 80% of the mother liquid was circulated to the step of crystallization and 20% thereof was discarded to the out side of system, the purity and the yield of purification were lowered.

The invention claimed is:

1. A method for the production of acrylic acid, comprising the steps of:
    a) introducing an acrylic acid-containing gas obtained by the reaction of catalytic gas phase oxidation of the raw material of acrylic acid into an absorption column and allowing the gas to contact with an absorbing aqueous solution thereby obtaining an acrylic acid-containing solution,
    b) supplying the acrylic acid-containing solution to a step of crystallization and separating the solution into acrylic acid and residual mother liquid having an acetic acid content of not less than 2 wt. %, and
    c) subjecting at least part of the residual mother liquid to distillation on a distillation column and circulating the distillate obtained by distillation to the absorption column of said step a), wherein the distillate is introduced onto the absorption column from a position different from the column top, thereby obtaining an acrylic acid-containing solution having a concentration of acrylic acid not less than 85 wt. % in the absorption column of step a).

2. A method according to claim 1, which further comprises a step of supplying the bottom liquid of the distillation column to an acrylic acid dimer decomposing device.

3. A method according to claim 1, wherein the acrylic acid-containing solution obtained at said step a) is treated for separation of acrolein contained therein and then the resultant acrylic acid-containing solution is introduced to said step b).

4. A method according to claim 1, wherein a bottom liquid of the distillation column is subjected to decomposition to obtain acrylic acid.

5. A method according to claim 1, wherein the distillate is introduced onto the absorption column from a position that provides a range of number of theoretical plates of 25–100, wherein theoretical plate 100 denotes the column bottom.

6. A method according to claim 1, wherein the distillate is introduced onto the column from a position that provides a range of number of theoretical plates of 50–100, wherein theoretical plate 100 denotes the column bottom.

7. A method for the production of acrylic acid, comprising the steps of
    a) reacting the raw material of acrylic acid by catalytic gas phase oxidation to obtain an acrylic acid-containing gas;
    b) contacting said acrylic acid-containing gas with an absorbing aqueous solution within an absorption column thereby obtaining an acrylic acid-containing solution;
    c) supplying said acrylic acid-containing solution to crystallization, whereby said acrylic acid-containing solution is separated into acrylic acid and residual mother liquid; and
    d) subjecting at least part of said residual mother liquid to distillation and circulating the distillate obtained to the absorption column of step b).

* * * * *